US012653460B2

(12) United States Patent
Gou et al.

(10) Patent No.: US 12,653,460 B2
(45) Date of Patent: Jun. 16, 2026

(54) METHOD AND APPARATUS OF LOCATING TUMOR

(71) Applicants: OUR UNITED CORPORATION, Shaanxi (CN); SHENZHEN OUR NEW MEDICAL TECHNOLOGIES DEVELOPMENT CO., LTD., Shenzhen (CN)

(72) Inventors: Tianchang Gou, Shaanxi (CN); Hao Yan, Shaanxi (CN)

(73) Assignees: OUR UNITED CORPORATION, Shaanxi (CN); SHENZHEN OUR NEW MEDICAL TECHNOLOGIES DEVELOPMENT CO., LTD., Shenzhen (CN)

( * ) Notice: Subject to any disclaimer, the term of this patent is extended or adjusted under 35 U.S.C. 154(b) by 1087 days.

(21) Appl. No.: 17/150,542

(22) Filed: Jan. 15, 2021

(65) Prior Publication Data

US 2021/0137454 A1    May 13, 2021

Related U.S. Application Data

(63) Continuation of application No. PCT/CN2018/096348, filed on Jul. 19, 2018.

(51) Int. Cl.
*A61B 5/11* (2006.01)
*A61B 5/00* (2006.01)
(Continued)

(52) U.S. Cl.
CPC ............ *A61B 5/4887* (2013.01); *A61B 90/39* (2016.02); *A61N 5/1037* (2013.01); *A61B 2090/3937* (2016.02)

(58) Field of Classification Search
None
See application file for complete search history.

(56) References Cited

U.S. PATENT DOCUMENTS 4,945,914 A * 8/1990 Allen ..................... A61B 90/10
606/54
5,588,430 A * 12/1996 Bova ........................ A61B 6/08
378/207
(Continued)

FOREIGN PATENT DOCUMENTS

CN        102697561 A        10/2012
CN        106139414 A        11/2016
(Continued)

OTHER PUBLICATIONS

Office Action, corresponding in Chinese patent application No. 201880006895.6, dated Jun. 30, 2022.
(Continued)

*Primary Examiner* — Tse W Chen
*Assistant Examiner* — Martin Nathan Ortega
(74) *Attorney, Agent, or Firm* — MARSHALL, GERSTEIN & BORUN LLP

(57) ABSTRACT

Embodiments of the present disclosure provide a method and an apparatus of locating a tumor. The method includes: obtaining a position of a positioning mark before the patient's head moves, a position of a positioning mark after the patient's head moves, and a position of the tumor before the patient's head moves, wherein the positioning mark is disposed at a preset position of the body surface of the patient's head; determining a position of the tumor after the patient's head moves according to the position of the positioning mark before the patient's head moves, the position of the positioning mark after the patient's head moves, and the position of the tumor before the patient's head moves.

5 Claims, 5 Drawing Sheets

(51) Int. Cl.
  *A61B 90/00*     (2016.01)
  *A61N 5/10*     (2006.01)

(56) References Cited

U.S. PATENT DOCUMENTS

| | | | | |
|---|---|---|---|---|
| 10,888,483 B2 * | 1/2021 | Ostyn | .................... | A61G 13/02 |
| 2002/0077545 A1 * | 6/2002 | Takahashi | ............ | A61N 5/1049 |
| | | | | 606/130 |
| 2005/0047544 A1 * | 3/2005 | Fu | .......................... | G06T 7/254 |
| | | | | 345/629 |
| 2007/0276229 A1 * | 11/2007 | Adler | .................. | A61B 6/0414 |
| | | | | 378/68 |
| 2008/0146905 A1 | 6/2008 | Keppel et al. | | |
| 2009/0110238 A1 * | 4/2009 | Li | .......................... | A61B 6/541 |
| | | | | 382/103 |
| 2010/0198101 A1 * | 8/2010 | Song | ................... | A61B 5/0871 |
| | | | | 600/547 |
| 2014/0125695 A1 * | 5/2014 | Lodron | ..................... | G06T 7/30 |
| | | | | 345/629 |
| 2014/0241497 A1 * | 8/2014 | Keall | ...................... | A61B 6/54 |
| | | | | 378/62 |
| 2014/0275698 A1 | 9/2014 | Lidstrom et al. | | |
| 2015/0031932 A1 | 1/2015 | Ge et al. | | |
| 2017/0319143 A1 * | 11/2017 | Yu | ......................... | A61B 5/682 |

FOREIGN PATENT DOCUMENTS

| | | |
|---|---|---|
| CN | 106730422 A | 5/2017 |
| CN | 106955122 A | 7/2017 |
| EP | 1624414 A1 | 2/2006 |
| KR | 101655910 B1 | 9/2016 |

OTHER PUBLICATIONS

Office Action, corresponding in Chinese patent application No. 201880006895.6, dated Nov. 3, 2021.
International Search Report and Written Opinion for Application No. PCT/CN2018/096348, dated Dec. 6, 2018.

* cited by examiner

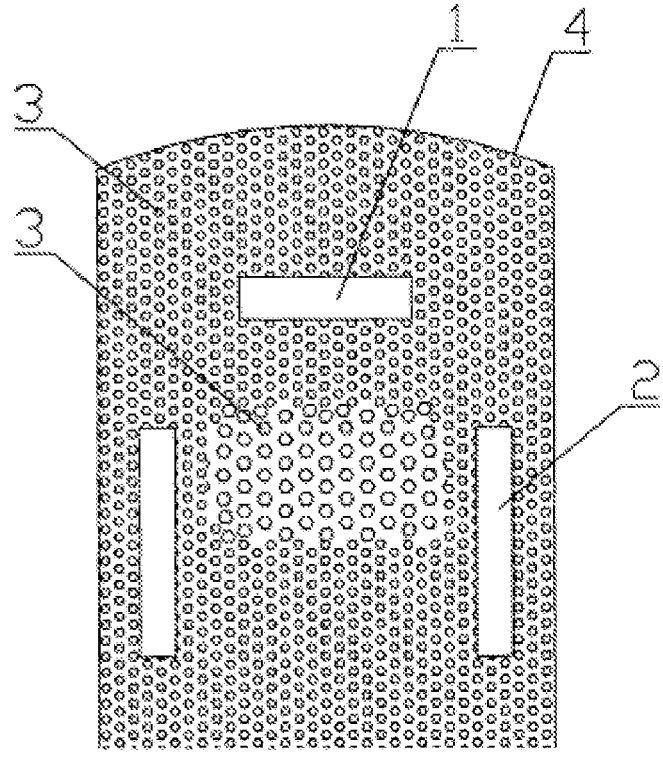

FIG. 1

| Obtaining a position of at least one positioning mark before the patient's head moves, a position of the at least one positioning mark after the patient's head moves, and a position of the tumor before the patient's head moves | S101 |

| Determining a position of the tumor after the patient's head moves according to the position of the at least one positioning mark before the patient's head moves, the position of the at least one positioning mark after the patient's head moves, and the position of the tumor before the patient's head moves. | S102 |

FIG. 2

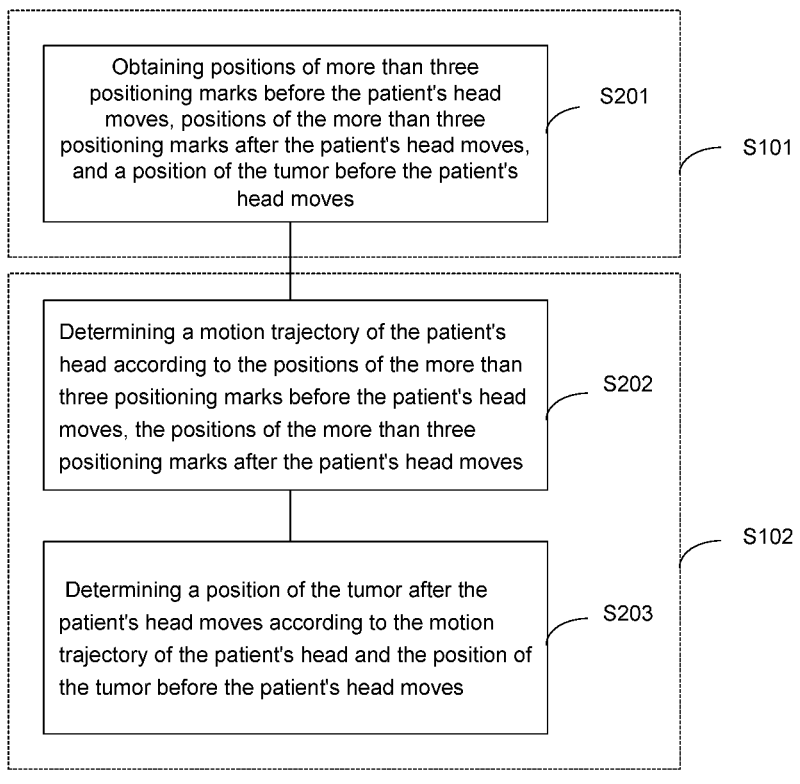

Obtaining positions of more than three positioning marks before the patient's head moves, positions of the more than three positioning marks after the patient's head moves, and a position of the tumor before the patient's head moves                S201

Determining a motion trajectory of the patient's head according to the positions of the more than three positioning marks before the patient's head moves, the positions of the more than three positioning marks after the patient's head moves                S202

Determining a position of the tumor after the patient's head moves according to the motion trajectory of the patient's head and the position of the tumor before the patient's head moves                S203

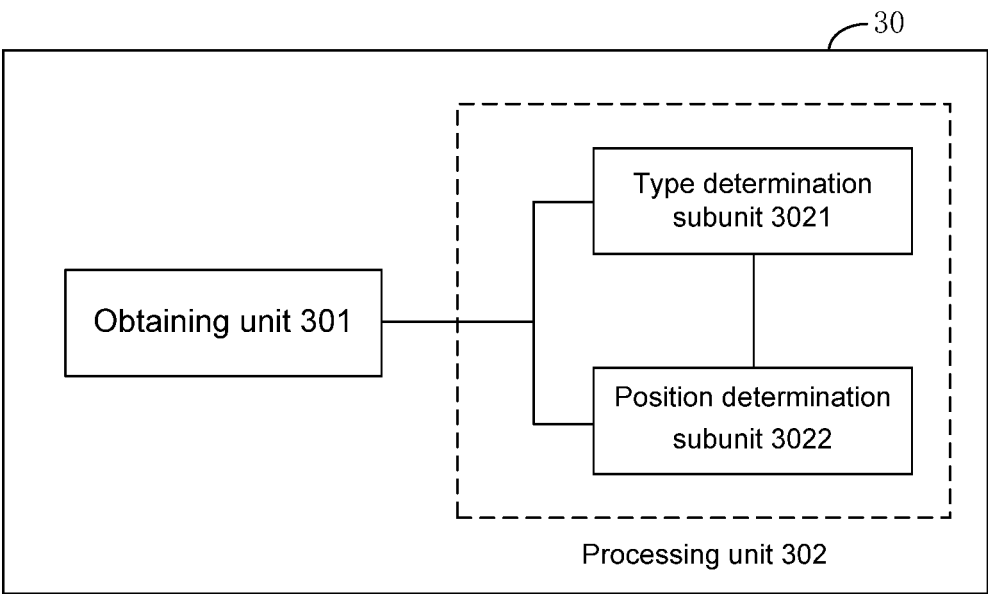

30

Obtaining unit 301

Type determination subunit 3021

Position determination subunit 3022

Processing unit 302

401
Storage unit

402
Processing unit

403
Interface unit

503
Transceiver

502
Processor

504

501
Memory

METHOD AND APPARATUS OF LOCATING TUMOR

CROSS-REFERENCE TO RELATED APPLICATION

This application is a Bypass Continuation Application of PCT/CN2018/096348 filed on Jul. 19, 2018, and the entirety of each is incorporated herein by reference.

TECHNICAL FIELD

The disclosure relates to the field of medical instruments, and in particular, to a method and an apparatus of locating a tumor.

BACKGROUND

At present, radiation therapy is a method of treating tumors using radioactive rays, which may cause complete necrosis or apoptosis of cancer cells, and is one of the main means for treating malignant tumors. During radiation therapy, it is necessary to locate the patient's tumor at the position of isocenter, i.e., an intersection of the radioactive rays, so that the radioactive rays pass through the tumors to kill the tumor tissues. If there is a deviation in the position of the tumor, it will not only cause the tumor cells not to be effectively killed, increase the risk of secondary cancer, but also cause damage to healthy parts. As a result, one of the key technologies of radiation therapy is to maintain an accurate position of the tumor during treatment.

At present, in the prior art, in order to accurately locate the tumor at the isocenter during the radiation therapy of the tumor, it is first necessary for the patient to be given a computed tomography (CT) to obtain the CT image to determine the position, size, shape, and surrounding tissues of the tumor. And then the patient's head is fixed using a treatment head frame during the treatment to locate the tumor at the isocenter of the radiotherapy device.

In the method of locating using the treatment head frame, four studs disposed in the treatment head frame need to be fixed on the skull of the patient's head through the human skin, and the movement of the tumor is avoided during the treatment by fixing the position of the patient's head. After the treatment is finished, the studs are removed. This method is called an invasive location, and it will cause great damage to the patient, although the location accuracy thereof is high.

In addition, compared with the above-mentioned invasive location, the related art also provides a non-invasive location method. Generally, in the non-invasive location method, the patient's head is fixed on the treatment couch through a head positioning mask, or the like. Compared with the above invasive location method, the non-invasive location method has a problem of instability, and the patient's head may still be moved.

Based on the above situation, the inventors believe that a more optimized method of locating the tumor is needed to eliminate the effect of the positional change of the patient's head on the tumor location result.

SUMMARY

The embodiments of the disclosure provide a method and an apparatus of locating a tumor, which can eliminate the effect of the positional change of the patient's head on the tumor location result, and improve the accuracy of the tumor location.

In order to achieve the above objective, the embodiments of the present disclosure adopt the following technical solutions.

In a first aspect, the embodiments of the present disclosure provide a method of locating a tumor, which is applied to locating a tumor in a patient's head, and the method includes: obtaining a position of positioning mark before the patient's head moves, the position of the positioning mark after the patient's head moves, and the position of the tumor before the patient's head moves, and the positioning mark is disposed at a preset position of the body surface of the patient's head; and determining the position of the tumor after the patient's head moves according to the position of the positioning mark before the patient's head moves, the position of the positioning mark after the patient's head moves, and the position of the tumor before the patient's head moves.

In a second aspect, the embodiments of the present disclosure provide an apparatus of locating a tumor, which includes: a processor, a memory, a bus and a communication interface. The memory is configured to store computer execution instructions. The processor is connected to the memory through the bus, and when a cache server is running, the processor executes the computer execution instructions stored by the memory to cause the apparatus of locating a tumor to execute the method of locating a tumor as provided in the above first aspect.

In a third aspect, the embodiments of the present disclosure provide a computer storage medium, which includes instructions, and when the instructions are run on a computer, the computer is caused to execute the method of locating a tumor as provided in the above first aspect.

In a fourth aspect, the embodiments of the present disclosure provide a computer program product including instructions, and when the instructions are run on a computer, the computer is caused to execute the method of locating a tumor as provided in the above first aspect.

BRIEF DESCRIPTION OF THE DRAWINGS

In order to more clearly illustrate the embodiments of the present disclosure or the technical solutions in the prior art, the drawings used in the description of the embodiments or the prior art will be briefly described below. Obviously, the drawings in the following description are only some embodiments of the present disclosure, and a person of ordinary skill in the art can obtain other drawings according to these drawings without paying any creative effort.

FIG. 1 is a schematic diagram showing a structure of a head locating mask in the prior art;

FIG. 2 is a flow diagram of a method of locating a tumor, according to embodiments of the present disclosure;

FIG. 6 is a flow diagram of another method of locating a tumor, according to embodiments of the present disclosure;

FIG. 7 is a schematic diagram showing a structure of an apparatus of locating a tumor, according to embodiments of the present disclosure;

FIG. 8 is a schematic diagram showing a structure of another apparatus of locating a tumor, according to embodiments of the present disclosure; and FIG. 9 is a schematic diagram showing a structure of yet another apparatus of locating a tumor, according to embodiments of the present disclosure.

DETAILED DESCRIPTION

Figure 3:
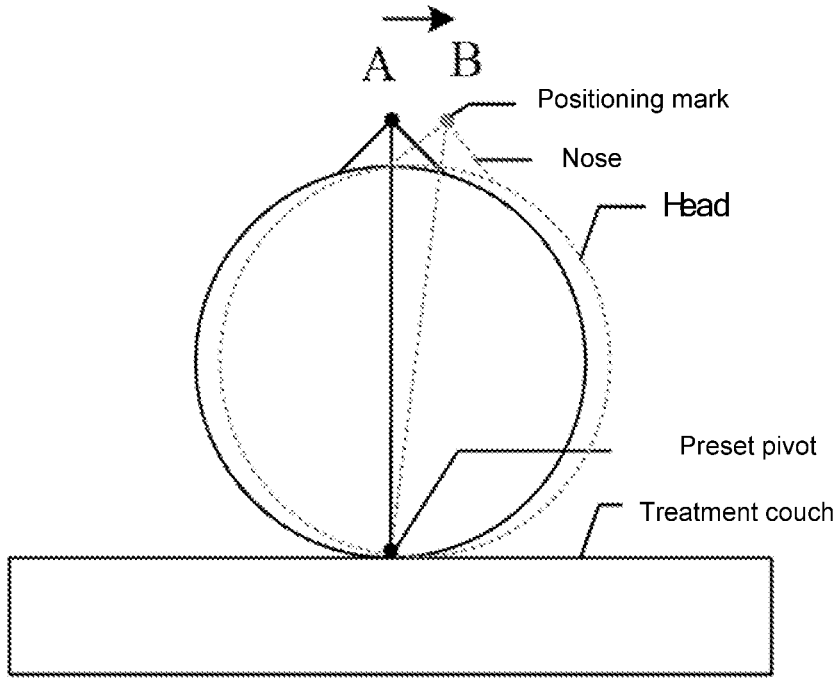
FIG. 3 is a schematic diagram showing movement of a patient's head.

The embodiments of the present disclosure will be described in the following with reference to the accompanying drawings. The present disclosure is applied to locate a tumor in a patient's head.

First, the technical terms involved in the embodiments of the present disclosure are introduced.

A locating mask, which is a new functional medical material with a memory function, and is made of a high-molecular polymer low-temperature thermoplastic plate. The locating mask is widely used for auxiliary locating and fixing the patients with tumors in the radiation therapy, so as to reduce unnecessary damage to normal tissues caused by the movement of the patient's body, which improves the absorption of local lesions on the rays. Specifically, according to different fixed positions, the locating mask may be classified into a head locating mask, a chest locating mask, an abdominal locating mask, and a body locating mask. FIG. 1 is a schematic diagram showing a structure of a head locating mask. As shown in FIG. 1, the head locating mask includes a low-temperature thermoplastic plate body 4, and there is a through hole 1 at a position of an upper middle portion of the low-temperature thermoplastic plate body corresponding to the nose. Both sides of the low-temperature thermoplastic plate body are provided with a mounting groove, a reinforcing rib 2 is fixed in the mounting groove, and meshes 3 are distributed on the low-temperature thermoplastic plate body other than the through hole 1 and the reinforcing rib 2. When the head locating mask is used, the patient should first lie on the treatment couch, then the head locating mask is placed over the patient's face, and then the patient's head is fixed to the treatment couch through thermoforming of the head locating mask.

A locating dental tray, which is a functional medical material, and is used for auxiliary locating and fixing the patients with tumors in the radiation therapy. During the radiation therapy, the patient bites the locating dental tray, so that the positions of the patient's head and the treatment device are relatively fixed.

The full name of IGRT is image guided radiation therapy. The IGRT is a four-dimensional radiation therapy technology. This locating method is to scan a 3D image of the entire patient's head through ray irradiation, thereby realizing locating the tumor.

The inventive concept of the present disclosure will be described below.

In the embodiments of the present disclosure, in view of accurately locating the tumor in the process of radiation therapy in the prior art, the patient's head is usually fixed, thereby eliminating the effect of the positional change of the patient's head on the accuracy of the tumor locating. However, when the patient's head is fixed, especially when the patient's head is fixed through the means of non-invasive locating, the patient's head may still be moved. For example, when a head locating mask is used for fixation, the patient's head often rotates around a contact point of the head and the treatment couch. When a locating dental tray is used for fixation, the patient's head often rotates around an axis of the dental tray. In this case, the position of the tumor will be affected. For this problem, the internal structure image of the entire patient's head is scanned through ray irradiation in the IGRT technology, thereby realizing locating the tumor. However, this locating method will cause additional radiation damage to the patient, and the IGRT device is also expensive, so the treatment cost is high.

Further, based on the characteristic that the head of the human body only performs rigid movement, the inventors of the present disclosure conceive that the overall movement of the patient's head can be known by collecting the positional change situation of positioning marks on the body surface of the patient's head. And then it is also possible to know the positional change situation of the tumor, thereby achieving precise locating of the tumor.

Based on the above inventive concept, the embodiments of the disclosure provide a method of locating a tumor, which can eliminate the effect of the positional change of the patient's head on the tumor locating result, and improve the accuracy of the tumor locating. The following embodiments 1 to 4 are provided for reference.

Embodiment 1

The embodiment of the present disclosure provides a method of locating a tumor. As shown in FIG. 2, the method includes the following steps.

In S101, a position of a positioning mark before the patient's head moves, the position of the positioning mark after the patient's head moves, and the position of the tumor before the patient's head moves are obtained.

The positioning mark is disposed at a preset position of the body surface of the patient's head.

For example, the positioning mark in the embodiments of the present disclosure may be optical positioning mark, such as infrared positioning balls. The infrared positioning ball may be attached to the patient's nasal tip, the junction of the ear and the cheek, or the like. Through an optical tracking system, such as an infrared tracking system, the motion of the optical positioning mark may be tracked in time, and then the position of the positioning mark before and after the patient's head moves are obtained.

In addition, the position of the tumor before the patient's head moves may be obtained by calculating the relative position of the tumor in the patient's head through the CT image, and further obtaining the positional information such as the position coordinate of the tumor.

In S102, the position of the tumor after the patient's head moves is determined according to the position of the positioning mark before the patient's head moves, the position of the positioning marks after the patient's head moves, and the position of the tumor before the patient's head moves.

Since the head of the human body is a whole, and it can only perform rigid movement, the movement situation of the patient's head may be obtained after obtaining the positional change of at least one positioning mark on the body surface of the head, and then the position of the tumor after the patient's head moves may be obtained after knowing the position of the tumor before the patient's head moves.

In one implementation manner, S102 may specifically include the following step 102a (S102a) and step 102b (S102b).

In S102a, the motion type of the patient's head is determined according to the position of the positioning mark before the patient's head moves, and the position of the positioning mark after the patient's head moves; and the motion type at least includes one or two of translation and rotation around a preset pivot.

The S102a may include: determining movement amount of the positioning mark according to the position of the positioning mark before the patient's head moves, and the position of the positioning mark after the patient's head moves; and determining the motion type of the patient's head according to the movement amount of the positioning mark.

When radiation therapy is performed on the tumor of the patient's head, the patient's head is usually fixed to the treatment couch through the locating mask or the locating dental tray. In this case, the patient's head may rotate around the pivot. In rare cases, the patient's head may also move horizontally.

For example, a translation vector of each positioning mark may be calculated according to three-dimensional coordinates of at least two positioning marks in the three-dimensional space before and after the at least two positioning marks move. If the translation vector of each mark is the same or approximately the same, the motion type of the patient's head is determined to be translation.

When the translational motion of the patient's head is excluded, it can be known that the patient's head rotates around the pivot. In this case, the motion type of the patient's head is determined according to the fixation mode of the patient's head. For example, if a mask is used for fixation, the motion mode of the patient's head is to rotate around the preset pivot at the back of the patient's head. If the dental tray is used for fixation, the motion mode of the patient's head is to rotate around the preset pivot at the dental tray. Of course, it is also possible to continue to determine which pivot the patient's head is rotated around according to a geometric transformation relationship of at least three positioning marks in the three-dimensional space.

As a result, the positioning mark in the embodiments of the present disclosure may specifically include a plurality of positioning marks, and then S102a includes: determining movement amount of the positioning marks according to the positions of the plurality of positioning marks before the patient's head moves, and the positions of the plurality of positioning marks after the patient's head moves; and determining the motion type of the patient's head according to the movement amount of the positioning marks.

In S102b, the position of the tumor after the patient's head moves is determined according to the motion type of the patient's head and the position of the tumor before the patient's head moves.

After determining the motion type of the patient's head, the position of the tumor needs to be calculated based on different motion types that the patient's head performs.

In one implementation manner, in a case where it is determined that the motion type of the patient's head is translation, S102b includes: determining the position of the tumor after the patient's head moves according to movement amount of the plurality of positioning marks and the position of the tumor before the patient's head moves.

For example, positions of at least two positioning marks before the patient's head moves, and positions of the at least two positioning marks after the patient's head moves are obtained. The at least two positioning marks are disposed at different preset positions of the body surface of the patient's head. A translation vector of a first positioning mark and a translation vector of a second positioning mark are calculated. It is determined whether there is translation in the patient's head according to the translation vector of the first positioning mark and the translation vector of the second positioning mark. In a case where it is determined that there is translational movement in the patient's head, a translation vector of the patient's head is calculated, and the coordinate of the coordinate point of the tumor in a space coordinate system after the patient's head moves is calculated according to the translational vector of the patient's head and the coordinate value of the coordinate point of the tumor in the space coordinate system before the patient's head moves.

In one implementation manner, in a case where it is determined that the motion type of the patient's head is rotation around a preset pivot, S102b includes step 102b-1 (S102b-1) to step 102b-3 (S102b-3).

In S102b-1, whether the position of the tumor before the patient's head moves coincides with the preset pivot is determined.

In S102b-2, In a case where it is determined that the position of the tumor before the patient's head moves coincides with the preset pivot, the position of the tumor after the patient's head moves is still the position of the tumor before the patient's head moves.

When the patient lies on the treatment couch, the patient's head is fixed by a positioning mask on the preset pivot of the treatment couch. As a result, when the patient's head rotates around the preset pivot, and in a case where the position of the tumor coincides with the preset pivot, there is no relative movement between the patient's head and the preset pivot. As a result, the position of the tumor does not move with the movement of the patient's head. FIG. 3 is a schematic diagram of movement of the patient's head, wherein a solid line portion in FIG. 3 is the position of the patient's head before the patient's head moves, and a dotted line portion is the position of the patient's head after the patient's head moves. It can be seen that the position of the tumor does not move as the patient's head moves when the position of the tumor coincides with the preset pivot. As a result, in the embodiments of the present disclosure, after determining that the position of the tumor coincides with the preset pivot, it can be known that the position of the tumor after the patient's head moves is still the position of the tumor before the patient's head moves.

In S102b-3, in a case where it is determined that the position of the tumor before the patient's head moves does not coincide with the preset pivot, the position of the tumor after the patient's head moves is determined according to the position of the positioning mark before the patient's head moves, the position of the positioning mark after the patient's head moves, and the position of the tumor before the patient's head moves.

In one implementation manner, S101 includes: obtaining a coordinate value $(X_A, Y_A, Z_A)$ of the coordinate point A of the first positioning mark in the spatial coordinate system before the patient's head moves, a coordinate value $(X_B, Y_B, Z_B)$ of the coordinate point B of the first positioning mark in the spatial coordinate system after the patient's head moves, and a coordinate value $(X_C, Y_C, Z_C)$ of the coordinate point C of the tumor in the space coordinate system before the patient's head moves.

The spatial coordinate system is a coordinate system established relative to the treatment couch, and the preset pivot is the origin O of the spatial coordinate system.

Figure 4:
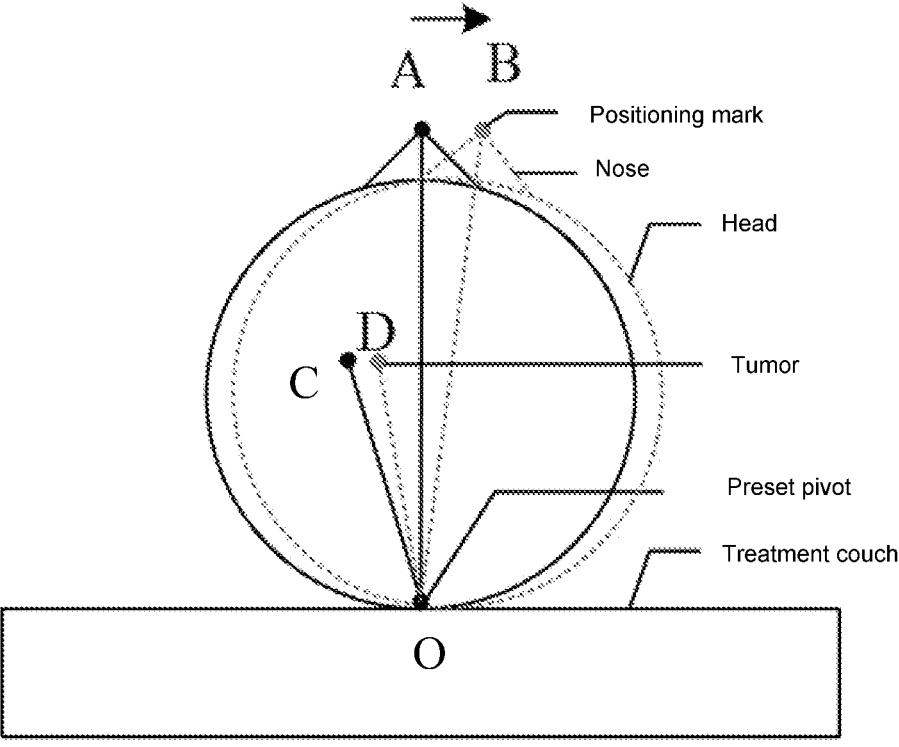
FIG. 4 is another schematic diagram showing movement of a patient's head.

For example, FIG. 4 is a schematic diagram of movement of the patient's head. The solid line portion in FIG. 4 is the position of the patient's head before the patient's head moves, and the dotted line portion is the position of the patient's head after the patient's head moves. The point A is the position of the first positioning mark before the patient's head moves, and the point B is the position of the first positioning mark after the patient's head moves. The point C is the position of the tumor before the patient's head moves, and the point D is the position of the tumor after the patient's head moves. In the exemplary figure, the first positioning mark is attached to the nasal tip of the head. The point O is the preset pivot.

Figure 5:
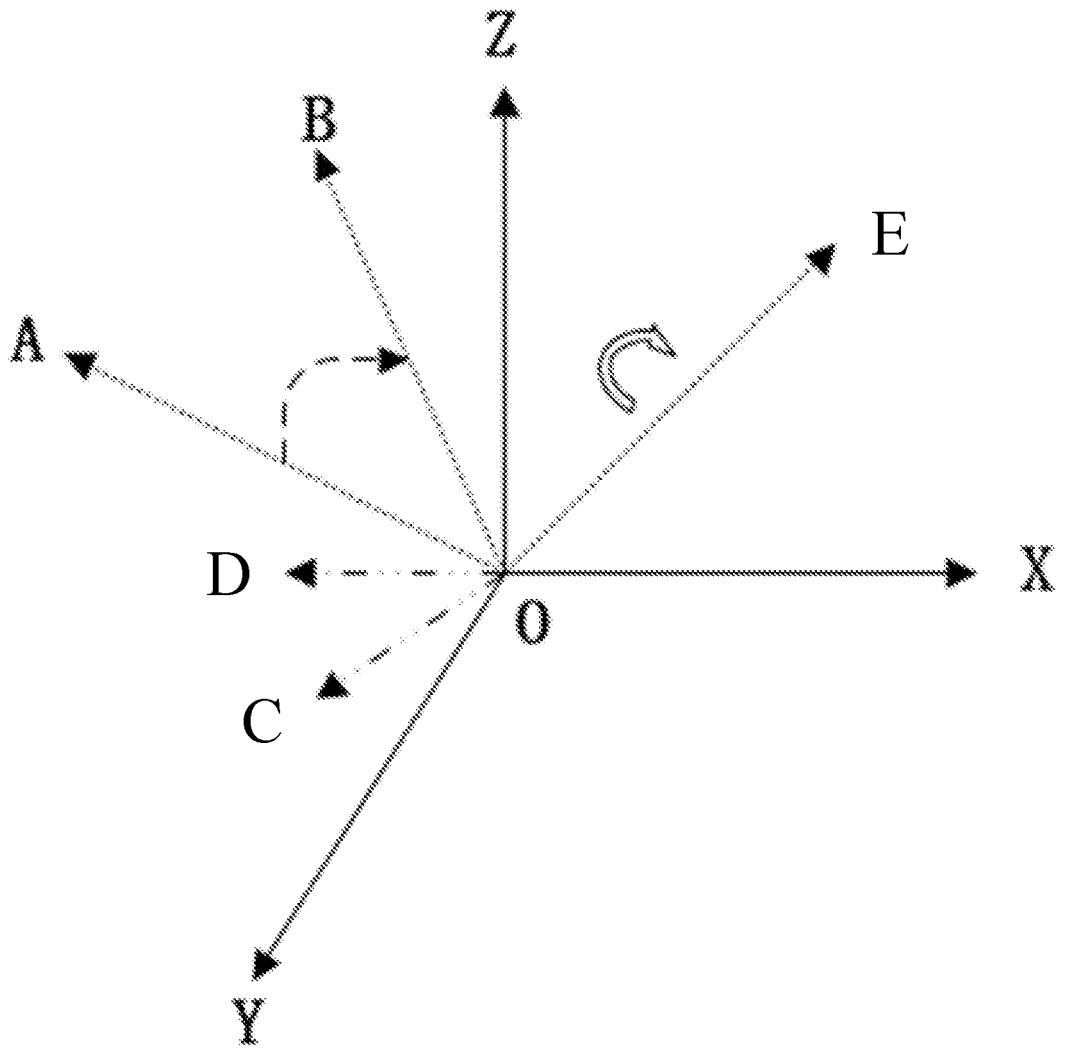
FIG. 5 is a schematic diagram of establishing a coordinate system corresponding to a treatment couch at an origin O of a space coordinate system with a preset pivot, according to embodiments of the present disclosure.

Further, as shown in FIG. 5, a space coordinate system corresponding to the treatment couch is established by taking the preset pivot as the origin O of the space coordinate system. A is the position of the first positioning mark before the head moves $(X_A, Y_A, Z_A)$, and B is the position of the first positioning mark after the head moves $(X_B, Y_B, Z_B)$. C is the position of the tumor before the head moves $(X_C, Y_C, Z_C)$, and D is the position of the tumor after the head moves $(X_D, Y_D, Z_D)$. Vector OE is a normal vector of a plane formed by the vector OA and the vector OB. The coordinates of A and B are detected by the optical tracking system to obtain the corresponding coordinate positions. The coordinate position of C is calculated from the relative relationship between the tumor and the pivot in the CT image. As a result, as long as the position of D is figured out, the motion of the tumor can be derived.

Further, S102*b*-3 may include: calculating the coordinate value $(X_D, Y_D, Z_D)$ of the coordinate point D of the tumor in the space coordinate system after the patient's head moves using the following formula 1:

$$\begin{bmatrix} X_D \\ Y_D \\ Z_D \\ 1 \end{bmatrix} = M * \begin{bmatrix} X_C \\ Y_C \\ Z_C \\ 1 \end{bmatrix}; \qquad \text{formula 1}$$

M represents a rotation matrix M corresponding to the vector OA rotated by an angle $\alpha$ around the vector OE and moved to the vector Oft the vector OE is the normal vector of a plane formed by the vector OA and the vector OB. The vector OA is a vector pointing from the origin O to the coordinate point A, the vector OB is a vector pointing from the origin O to the coordinate point B, and a is a degree of an angle ∠AB between the vector OA and the vector OB.

Further, a coordinate value of the coordinate point D of the tumor in the space coordinate system is calculated through formula 1 after the patient's head moves, which may include the following contents of steps (1)-(6).

(1) The vector OE is obtained by doing a cross-product of the vector OA and the vector Oft so the vector OE is:

$$(Y_A*Z_B - Z_A*Y_B, Z_A*X_B X_A*Z_B, X_A*Y_B - Y_A*X_B)$$

(2) The degree of the angle ∠AB between the vector OA and the vector OB is:

$$\angle AB = a\cos\left(\frac{OA*OB}{|OA|*|OB|}\right)$$

(3) In the embodiments of the present disclosure, since there is only rigid transformation in the human head, and after the head is fixed on the treatment couch by a positioning mask, the head can only rotate around the preset pivot that serves as the origin. According to the principle of three-dimensional space transformation, any rigid transformation may be converted to a fixed angle rotated around any axis, that is, the degree of ∠AB rotated around the vector OE in this embodiment.

Further, the method of rotating around any axis may be divided into:

a. translating the rotation axis to coincide with the coordinate axis, and setting the corresponding operation as T;

b. rotating the degree of ∠AB, and setting the corresponding operation as R;

c. translating the rotation axis back to the original position, and setting corresponding operation as $T^{-1}$;

that is, the whole processes being $P'=P \cdot T \cdot R \cdot T^{-1}$.

(4) According to the rotation rule of the right-handed coordinate system, the rotation matrix in the three-dimensional space includes:

a rotation matrix when rotating around the X axis by $\beta$ degrees:

$$R_x(\beta) = \begin{bmatrix} 1 & 0 & 0 & 0 \\ 0 & \cos(\beta) & -\sin(\beta) & 0 \\ 0 & \sin(\beta) & \cos(\beta) & 0 \\ 0 & 0 & 0 & 1 \end{bmatrix}$$

a rotation matrix when rotating around the Y axis by $\beta$ degrees:

$$R_y(\beta) = \begin{bmatrix} \cos(\beta) & 0 & \sin(-\beta) & 0 \\ 0 & 1 & 0 & 0 \\ -\sin(-\beta) & 0 & \cos(\beta) & 0 \\ 0 & 0 & 0 & 1 \end{bmatrix}$$

a rotation matrix when rotating around the Z axis by $\beta$ degrees:

$$R_z(\beta) = \begin{bmatrix} \cos(\beta) & \sin(\beta) & 0 & 0 \\ -\sin(\beta) & \cos(\beta) & 0 & 0 \\ 0 & 0 & 1 & 0 \\ 0 & 0 & 0 & 1 \end{bmatrix}$$

(5) Based on the content of step (4), it can be known that the rotation matrix M rotated around the vector OE by a degrees according to the rotation rule of the right-hand coordinate system is:

$$M = R_x(\gamma) \cdot R_z(-\theta) \cdot R_y(\alpha) \cdot R_z(\theta) \cdot R_x(-\gamma)$$

wherein $\gamma$ is an angle at which the vector OE is rotated around the X-axis to the XOY plane, and $\theta$ is an angle at which the OE vector that has been rotated to the XOY plane is rotated around Z-axis to coincide with the Y-axis, and a is an angle ∠AB between the vector OA and the vector OB.

(6) Further, according to formula 1, that is:

$$\begin{bmatrix} X_D \\ Y_D \\ Z_D \\ 1 \end{bmatrix} = M * \begin{bmatrix} X_C \\ Y_C \\ Z_C \\ 1 \end{bmatrix}$$

the Euclidean distance between point C and point D may be calculated and the motion situation of the tumor may be analyzed.

In the embodiments of the present disclosure, when the patient's head is fixed on the treatment couch through the positioning mask, the patient's head rotates around the preset pivot, but there is often no relative movement at the contact point between the patient's head and the treatment couch. As a result, it is possible to determine the positional change situation of the tumor by obtaining the positional change situation of one positioning mark. Further, by obtaining the coordinate value of the first positioning mark in the spatial coordinate system before and after the head moves, a rotation matrix M of the head is calculated, and then the rotation matrix M is used to calculate the coordinate value $(X_D, Y_D, Z_D)$ of the coordinate point D of the tumor in the spatial coordinate system to achieve precise positioning of the tumor.

Embodiment 2

In one implementation manner, the motion trajectory of the patient's head may be determined directly according to geometric transformation relationship in space of at least three positioning marks that are not on a same straight line. Based on the method provided in the embodiment 1, the number of the positioning marks is more than three, and the more than three positioning marks are disposed at different preset positions of the body surface of the patient's head, and the more than three positioning marks are not on a same line. As shown in FIG. 6, the method provided by the embodiments of the present disclosure may further include:

S101, which corresponds to S201 in embodiment 2.

In S201, positions of more than three positioning marks before the patient's head moves, positions of the more than three positioning marks after the patient's head moves, and the position of the tumor before the patient's head moves are obtained.

The more than three positioning marks are disposed at different preset positions of the body surface of the patient's head, and the more than three positioning marks are not on the same line.

S102 may include the following step 202 (S202) to step 203 (S203).

In S202, the movement trajectory of the patient's head is determined according to the positions of the more than three positioning marks before the patient's head moves, the positions of the more than three positioning marks after the patient's head moves.

In S203, the position of the tumor after the patient's head moves is determined according to the motion trajectory of the patient's head and the position of the tumor before the patient's head moves.

Embodiment 3

The embodiments of the present disclosure further provide an apparatus of locating a tumor based on the method of locating a tumor provided by the above embodiments. As shown in FIG. 7, the apparatus 30 of locating a tumor includes:

an obtaining unit 301, which is configured to obtain the position of the positioning mark before the patient's head moves, the positions of the positioning mark after the patient's head moves, and the position of the tumor before the patient's head moves; the positioning mark is disposed at the preset position of the body surface of the patient's head;

a processing unit 302, which is configured to determine the position of the tumor after the patient's head moves according to the position of the positioning mark before the patient's head moves, the position of the positioning mark after the patient's head moves, and the position of the tumor before the patient's head moves, after the obtaining unit obtains the position of the positioning mark before the patient's head moves, the position of the positioning mark after the patient's head moves, and the position of the tumor before the patient's head moves.

For example, as shown in FIG. 7, the processing unit 302 includes: a type determination subunit 3021 and a position determination subunit 3022.

The type determination subunit 3021 is configured to determine the motion type of the patient's head according to the position of the positioning mark before the patient's head moves, and the position of the positioning mark after the patient's head moves. The motion type at least includes one or two of translation and rotation around a preset pivot.

The position determination subunit 3022 is configured to determine the position of the tumor after the patient's head moves according to the motion type of the patient's head and the position of the tumor before the patient's head moves.

For example, the type determination subunit 3021 is configured to determine movement amount of the positioning mark according to the position of the positioning mark before the patient's head moves, and the position of the positioning mark after the patient's head moves; and to determine the motion type of the patient's head according to the movement amount of the positioning mark.

For example, the position determination subunit 3022 is configured to determine the position of the tumor after the patient's head moves according to the movement amount of the positioning mark and the position of the tumor before the patient's head moves, in a case where it is determined that the motion type of the patient's head is translation.

For example, the position determination subunit 3022 is configured to determine whether the position of the tumor before the patient's head moves coincides with the preset pivot, in a case where it is determined that the motion type of the patient's head is rotation around the preset pivot. On one hand, in a case where it is determined that the position of the tumor before the patient's head moves coincides with the preset pivot, the position of the tumor after the patient's head moves is still the position of the tumor before the patient's head moves. On the other hand, in a case where it is determined that the position of the tumor before the patient's head moves does coincides with the preset pivot, the position of the tumor after the patient's head moves is determined according to the position of the positioning mark before the patient's head moves, the position of the positioning mark after the patient's head moves, and the position of the tumor before the patient's head moves.

For example, the number of the positioning marks is more than three, and the more than three positioning marks are disposed at different preset positions of the body surface of the patient's head, and the more than three positioning marks are not on a same line.

Since the apparatus of locating a tumor in the embodiments of the present disclosure may be applied to implement the above-mentioned method embodiments, the technical effects that may be obtained can also be referred to the foregoing method embodiments, which will not be described in the embodiment again.

Figures 8, 9:
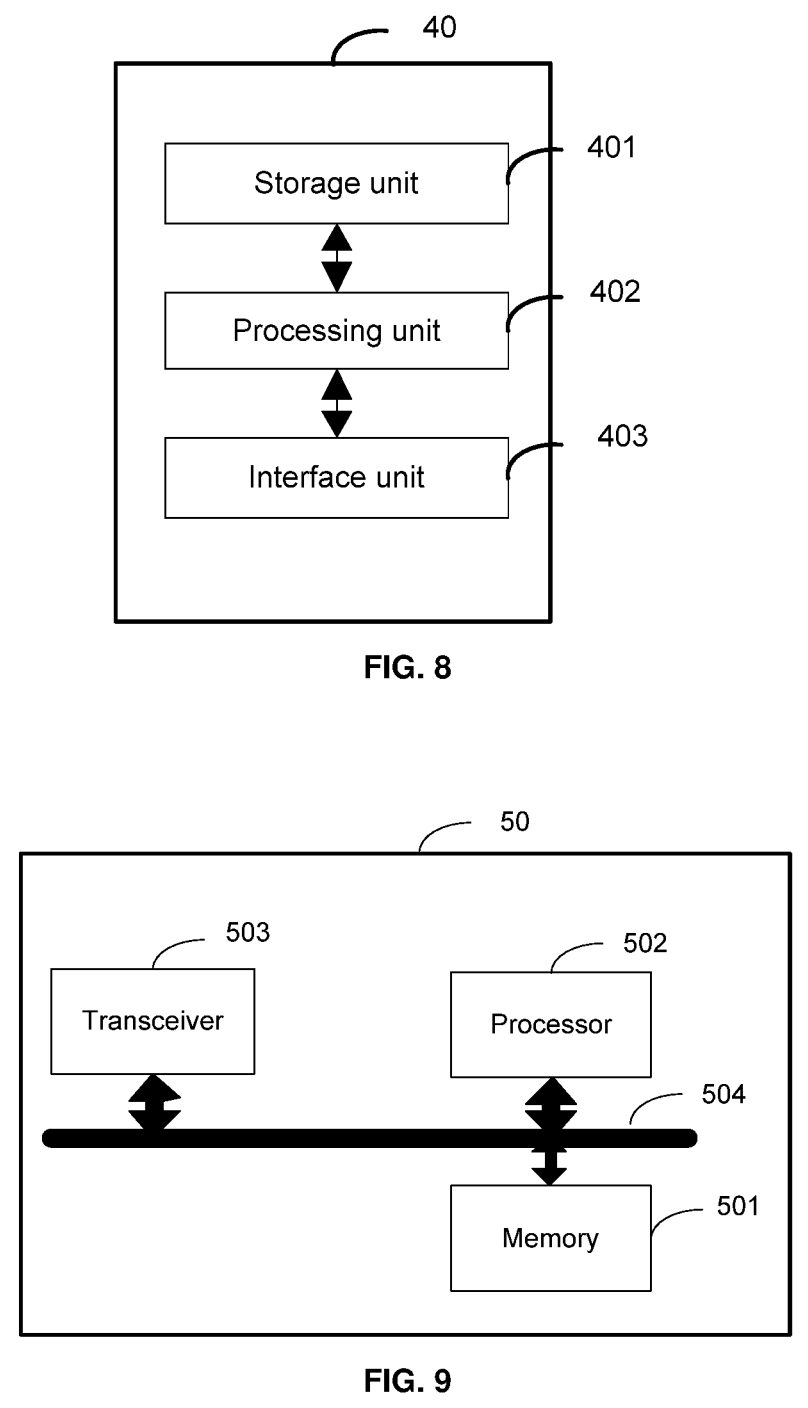

In a case where an integrated unit is adopted, FIG. 8 shows a possible schematic diagram showing the structure of the above apparatus of locating a tumor. The apparatus 40 of locating a tumor includes a storage unit 401, a processing unit 402, and an interface unit 403. The processing unit 402 is used for controlling and managing actions of the apparatus 40 of positioning a tumor.

For example, the processing unit is a processor, the storage unit is a memory, and the interface unit is a transceiver. Further, the apparatus of positioning a tumor 50 shown in FIG. 9 includes a transceiver 503, a processor 502, a memory 501, and a bus 504. The transceiver 503 and the processor 502 are connected to the memory 501 via the bus 504.

The processor 502 may be a general-purpose central processing unit (CPU), a microprocessor, an application-specific integrated circuit (ASIC), or one or more integrated circuits for controlling the execution of the program of the present disclosure.

The memory 501 may be a read-only memory (ROM) or any other types of static storage devices that can store static information and instructions, a random access memory (RAM) or any other types of dynamic storage devices that can store information and instructions. The memory 501 may also be an electrically erasable programmable read-only memory (EEPROM), a compact disc read-only memory (CD-ROM), or any other magnetic storage devices such as optical disc storage, disc storage (including compact discs, laser discs, optical discs, digital versatile discs, blu-ray discs, etc.), or a disk storage medium, or any other medium that can be used to carry or store desired program code in a form of instructions or data structures and can be accessed by a computer, which is not limited thereto. The memory may exist independently and be connected to the processor via a bus. The memory may also be integrated with the processor.

The memory 501 is used to store application program codes for executing the solutions of the present disclosure, which is controlled by the processor 502 for execution. The transceiver 503 is configured to receive the content input by an external device, and the processor 502 is configured to execute the application program codes stored in the memory 501, thereby implementing the method of positioning a tumor described in the embodiments of the present disclosure.

The above embodiments may be implemented in whole or in part through software, hardware, firmware, or any combination thereof. When implemented by using a software program, the embodiments may be implemented in whole or in part in the form of a computer program product. The computer program product includes one or more computer instructions. When the computer program instructions are loaded and executed on the computer, the processes or functions described are generated in whole or in part in accordance with embodiments of the present disclosure. The computer can be a general purpose computer, a special purpose computer, a computer network, or any other programmable devices. The computer instructions can be stored in a computer readable storage medium or transferred from one computer readable storage medium to another computer readable storage medium. For example, the computer instructions can be transferred from a website site, computer, server or data center to another website site, computer, server, or data center by means of wired (e.g., coaxial cable, fiber optic, digital subscriber line (DSL)) or wireless (e.g., infrared, wireless, microwave, etc.) manner. The computer readable storage medium may be any available medium that can be accessed by the computer or a data storage device that includes one or more servers, data centers, or the like that can be integrated with a medium. The usable medium may be a magnetic medium (e.g., a floppy disk, a hard disk, a magnetic tape), an optical medium (e.g., a DVD), or a semiconductor medium (such as a solid state disk (SSD)), or the like.

The embodiments of the present disclosure further provide a non-transitory computer readable storage medium, which includes instructions, and when the instructions are run on a computer, the computer is caused to execute the method of positioning a tumor as provided in the above embodiments.

The embodiments of the present disclosure further provide a computer program product including instructions, and when the instructions are run on a computer, the computer is caused to execute the method of positioning a tumor positioning method as provided in the above embodiments.

The foregoing descriptions are merely specific implementation manners of the present disclosure, but the protection scope of the present disclosure is not limited thereto, and any person skilled in the art could readily conceive of changes or replacements within the technical scope of the present disclosure, which shall be included in the protection scope of the present disclosure. As a result, the protection scope of the present disclosure shall be subject to the protection scope of the claims.

What is claimed is:

1. A method of locating a tumor, wherein the method is applied to locate a tumor in a patient's head, and the method comprises:

obtaining, by a processor, a position of a positioning mark before the patient's head moves, a position of the positioning mark after the patient's head moves, and a position of the tumor before the patient's head moves, wherein the positioning mark is disposed at a preset position of a body surface of the patient's head;

determining, by the processor, movement amount of the positioning mark according to the position of the positioning mark before the patient's head moves, and the position of the positioning mark after the patient's head moves;

determining, by the processor, a motion type of the patient's head according to the movement amount of the positioning mark, wherein the motion type at least includes one or both of translation and rotation around a preset pivot; and determining, by the processor, a position of the tumor after the patient's head moves according to the motion type of the patient's head and the position of the tumor before the patient's head moves, wherein it is determined that the motion type of the patient's head is the translation, determining, by the processor, the position of the tumor after the patient's head moves according to the motion type of the patient's head, and the position of the tumor before the patient's head moves, includes:

determining, by the processor, the position of the tumor after the patient's head moves according to the movement amount of the positioning mark and the position of the tumor before the patient's head moves; or wherein it is determined that the motion type of the patient's head is the rotation around the preset pivot and that the position of the tumor before the patient's head moves coincides with the preset pivot, determining, by the processor, the position of the tumor after the patient's head moves according to the motion type of the patient's head, and the position of the tumor before the patient's head moves, includes:

determining, by the processor, that the position of the tumor after the patient's head moves is still the position of the tumor before the patient's head moves; or wherein it is determined that the motion type of the patient's head is the rotation around the preset pivot and that the position of the tumor before the patient's head moves does not coincide with the preset pivot, determining, by the processor, the position of the tumor after the patient's head moves according to the motion type of the patient's head, and the position of the tumor before the patient's head moves, includes:

determining, by the processor, the position of the tumor after the patient's head moves according to the position of the positioning mark before the patient's head moves, the position of the positioning mark after the patient's head moves, and the position of the tumor before the patient's head moves, wherein it is determined that the position of the tumor before the patient's head moves does not coincide with the preset pivot, and a space coordinate system is established by taking the preset pivot as an origin of the space coordinate system; and a position A of the positioning mark before the patient's head moves is $(X_A, Y_A, Z_A)$, a position B of the positioning mark after the patient's head moves is $(X_B, Y_B, Z_B)$, a position C of the tumor before the patient's head moves is $(X_C, Y_C, Z_C)$, and a position D of the tumor after the patient's head moves is $(X_D, Y_D, Z_D)$, and coordinates of the position C and the position D conform to the following formula:

$$\begin{bmatrix} X_D \\ Y_D \\ Z_D \\ 1 \end{bmatrix} = M * \begin{bmatrix} X_C \\ Y_C \\ Z_C \\ 1 \end{bmatrix}$$

wherein M is a rotation matrix corresponding to a vector OA rotated by an angle $\alpha$ around a vector OE and moved to a vector OB, $M=R_x(\gamma)\cdot R_z(-\theta)\cdot R_y(\alpha)\cdot R_z(\theta)\cdot R_x(-\gamma)$, the vector OE is a normal vector of a plane formed by the vector OA and the vector OB; and $\gamma$ is an angle at which the vector OE is rotated around an X-axis to an XOY plane, and $\theta$ is an angle at which the OE vector that has been rotated to the XOY plane is rotated around a Z-axis to coincide with a Y-axis, and a is an angle $\angle AB$ between the vector OA and the vector OB; $R_x(\gamma)$ is a rotation matrix when rotating around the X-axis by $\gamma$ degrees, $R_x(-\gamma)$ is a rotation matrix when rotating around the X-axis by $(-\gamma)$ degrees, $R_y(\alpha)$ is a rotation matrix when rotating around the Y-axis by $\alpha$ degrees, $R_z(-\theta)$ is a rotation matrix when rotating around the Z-axis by $(-\theta)$ degrees, and $R_z(\theta)$ is a rotation matrix when rotating around the Z-axis by $\theta$ degrees.

2. The method of locating a tumor according to claim 1, wherein there are more than three positioning marks, and the more than three positioning marks are disposed at different preset positions of the body surface of the patient's head, and the more than three positioning marks are not on a same line.

3. A non-transitory computer readable storage medium comprising instructions that, when run on a computer, cause the computer to execute the method of positioning a tumor according to claim 1.

4. An apparatus for locating a tumor, comprising a processor, a memory, a bus and a communication interface; wherein the apparatus is applied to locate a tumor of a patient's head;

the memory is configured to store computer execution instructions;

the communication interface is configured to obtain a position of a positioning mark before the patient's head moves, a position of the positioning mark after the patient's head moves, and a position of the tumor before the patient's head moves, and the positioning mark is disposed at a preset position of a body surface of the patient's head;

the processor is connected to the communication interface, and is connected to the memory through the bus; and the processor is configured to execute the computer execution instructions and determine movement amount of the positioning mark according to the position of the positioning mark before the patient's head moves, and the position of the positioning mark after the patient's head moves;

determine a motion type of the patient's head according to the movement amount of the positioning mark, wherein the motion type at least includes one or both of translation and rotation around a preset pivot; and determine a position of the tumor after the patient's head moves according to the motion type of the patient's head and the position of the tumor before the patient's head moves, wherein the processor is configured to execute the computer execution instructions, determine that the motion type of the patient's head is the translation, and determine the position of the tumor after the patient's head moves according to the movement amount of the positioning mark and the position of the tumor before the patient's head moves, or wherein the processor is configured to execute the computer execution instructions, and determine that the motion type of the patient's head is the rotation around the preset pivot and that the position of the tumor before the patient's head moves coincides with the preset pivot, and determine that the position of the tumor after the patient's head moves is still the position of the tumor before the patient's head moves; or wherein the processor is configured to execute the computer execution instructions, and determine that the motion type of the patient's head is the rotation around the preset pivot and that the position of the tumor before the patient's head moves does not coincide with the preset pivot, and determine the position of the tumor after the patient's head moves according to the position of the positioning mark before the patient's head moves, the position of the positioning mark after the patient's head moves, and the position of the tumor before the patient's head moves, wherein it is determined that the position of the tumor before the patient's head moves does not coincide with the preset pivot, and a space coordinate system is established by taking the preset pivot as an origin of the space coordinate system; and a position A of the positioning mark before the patient's head moves is $(X_A, Y_A, Z_A)$, a position B of the positioning mark after the patient's head moves is $(X_B, Y_B, Z_B)$, a position C of the tumor before the patient's head moves is $(X_C, Y_C, Z_C)$, and a position D of the tumor after the patient's head moves is $(X_D, Y_D, Z_D)$, and coordinates of the position C and the position D conform to the following formula:

$$\begin{bmatrix} X_D \\ Y_D \\ Z_D \\ 1 \end{bmatrix} = M^* \begin{bmatrix} X_C \\ Y_C \\ Z_C \\ 1 \end{bmatrix}$$

wherein M is a rotation matrix corresponding to a vector OA rotated by an angle $\alpha$ around a vector OE and moved to a vector OB, $M = R_x(\gamma) \cdot R_z(-\theta) \cdot R_y(\alpha) \cdot R_z(\theta) \cdot R_x(-\gamma)$, the vector OE is a normal vector of a plane formed by the vector OA and the vector OB; and $\gamma$ is an angle at which the vector OE is rotated around an X-axis to an XOY plane, and $\theta$ is an angle at which the OE vector that has been rotated to the XOY plane is rotated around a Z-axis to coincide with a Y-axis, and a is an angle $\angle AB$ between the vector OA and the vector OB; $R_x(\gamma)$ is a rotation matrix when rotating around the X-axis by $\gamma$ degrees, $R_x(-\gamma)$ is a rotation matrix when rotating around the X-axis by $(-\gamma)$ degrees, $R_y(\alpha)$ is a rotation matrix when rotating around the Y-axis by $\alpha$ degrees, $R_z(-\theta)$ is a rotation matrix when rotating around the Z-axis by $(-\theta)$ degrees, and $R_z(\theta)$ is a rotation matrix when rotating around the Z-axis by $\theta$ degrees.

5. The apparatus for locating a tumor according to claim 4, wherein there are more than three positioning marks, the more than three positioning marks are disposed at different preset positions of the body surface of the patient's head, and the more than three positioning marks are not on a same line.

\* \* \* \* \*